United States Patent [19]

Fernandez et al.

[11] 3,993,046

[45] Nov. 23, 1976

[54] SEIZURE SUPPRESSION DEVICE

[76] Inventors: Heriberto Fernandez, 1822 Gaston St., Winston-Salem, N.C. 27103; George T. Pardue, P.O. Box 131, Pilot Mountain, N.C. 27041

[22] Filed: Nov. 6, 1974

[21] Appl. No.: 521,402

[52] U.S. Cl. .............................................. 128/2.1 B
[51] Int. Cl.[2] ....................................... A61B 5/00
[58] Field of Search ................ 128/419 R, 421, 422, 128/1 C, 2.1 B, 2.1 R, 2.06 B, 2.06 R

[56] References Cited
UNITED STATES PATENTS

| | | | |
|---|---|---|---|
| 2,690,178 | 9/1954 | Bickford | 128/2.1 B |
| 3,753,433 | 8/1973 | Bakerich et al. | 128/2.1 B |
| 3,837,331 | 9/1974 | Ross | 128/2.1 B |
| 3,850,161 | 11/1974 | Liss | 128/2.1 B |
| 3,875,930 | 4/1975 | Silva et al. | 128/2.1 B |

*Primary Examiner*—William E. Kamm
*Attorney, Agent, or Firm*—Cushman, Darby & Cushman

[57] ABSTRACT

A method and apparatus for suppressing epileptic seizures whereby an EEG electrical signal from an epileptic is amplified, filtered to remove components above roughly 8 Hz and below 2 Hz, and applied to a level detector which produces a trigger signal when the EEG amplitude exceeds a predetermined, variable level. The gated signal operates an oscillator to produce a signal which is in turn applied to a speaker, such as a set of earphones, to produce an audio signal which is maintained for as long as the seizure lasts, and then for an additional 4 seconds.

17 Claims, 1 Drawing Figure

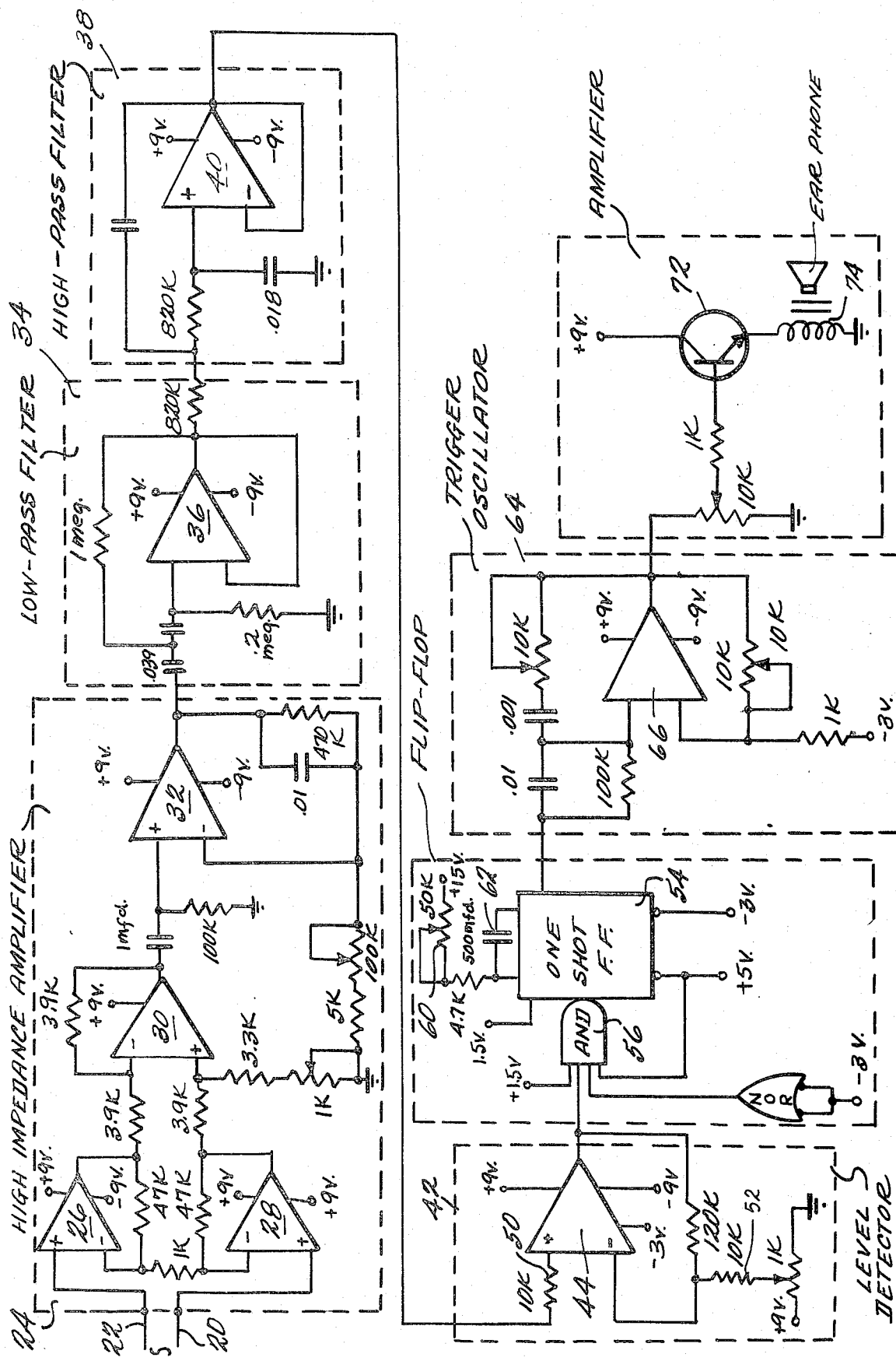

3,993,046

SEIZURE SUPPRESSION DEVICE

BRIEF DESCRIPTION OF THE PRIOR ART AND SUMMARY OF THE INVENTION

The invention relates to an apparatus and method for suppressing epileptic seizures.

Many techniques have been developed to at least partially suppress epileptic seizures so that epileptics may lead a normal or near normal life. The most common techniques involve the use of drugs. It has also been known for many years that an audio sound during a seizure will in some fashion suppress or at least partially suppress the seizure. It is also well known that during an epileptic seizure the EEG waveform of the epileptic includes relatively high amplitude spikes.

The present invention relates to an apparatus and method which is useful in at least partially suppressing or assisting in suppressing epileptic seizures. According to the apparatus and method of this application, the EEG waveform is applied to an electrical circuit which produces a trigger signal whenever the amplitude of the EEG signal exceeds a predetermined variable level, indicating that an epileptic seizure has begun or is imminent. This trigger signal is applied to an oscillator circuit which produces an electrical oscillatory signal preferably in the audio range, which is applied to a speaker such as a set of earphones on the patient to produce an audio tone which will interfere with the seizure and at least partially suppress it.

According to the specific circuitry described in detail below, the EEG signals derived conventionally from a pair of electrodes are amplified in a conventional high impedance amplifier and filtered by serially connected high pass and low pass filters to remove the frequency components above a first frequency and below a second frequency. The first frequency is preferably roughly 8 Hz while the second frequency is roughly 2 Hz since it is also known that the EEG signal during an epileptic seizure normally is within this frequency range. The filtered signal is then applied to a level detector and more particularly to one input to a differential amplifier having its other input connected to a source of voltage via a variable resistance to determine the level at which a trigger signal is produced. The output of the level detector is connected to a one-shot flip-flop also having a variable resistance connected to it which determines the time that the oscillator will remain operative following cessation of the trigger signal after the EEG waveform amplitude drops below the predetermined level. The one-shot flip-flop is in turn connected to a conventional trigger oscillator and the output of the oscillator, preferably an audio frequency for example of 1000 Hz, is connected to a set of earphones or other speaker via a conventional amplifier.

Many other objects and purposes of the invention will be clear from the detailed description of the drawing.

BRIEF DESCRIPTION OF THE DRAWING

The drawing illustrates one embodiment of the circuitry of this invention.

DETAILED DESCRIPTION OF THE DRAWING

Reference is now made to the FIGURE which illustrates one embodiment of the invention of this application. In this embodiment the conventional EEG signal from conventional electrodes is applied to lines 20 and 22 which are connected to the input to a conventional high impedance amplifier 24 which includes operational amplifiers 26, 28, 30 and 32.

The output of operational amplifier 32 is connected to the input of a conventional low pass filter 34 which includes operational amplifier 36 and which is preferably adjusted to remove frequency components of the EEG signal which are above 8 Hz. A second filter 38 which is a high pass filter is serially connected to the output of operational amplifier 36 and includes operational amplifier 40. Low pass filter 38 preferably includes components which have values so that frequency components in the EEG signal below 2 Hz are removed. As discussed briefly above, it is known that most epileptic seizure signals have a frequency in the range between 2 Hz and 8 Hz. The output of high pass filter 38 is applied to a conventional level detector 42 which includes operational amplifier 44 connected as a differential amplifier. Particularly the output of operational amplifier 40 is connected by resistor 50 to the negative input to amplifier 44 while the positive input is connected to a positive voltage source via variable resistance 52. Resistance 52 can be adjusted and establishes the level above which a trigger signal is produced. When the amplitude of the EEG signal exceeds the predetermined level set by variable resistor 52, operational amplifier 44 produces a trigger signal which is applied to a conventional one-shot flip-flop 54 by AND-gate 56. A variable resistor 60 is connected to one-shot flip-flop 54 and together with capacitor 62 defines a timing circuit determining the time interval of the pulse produced by one-shot flip-flop 54 and particularly the time following the cessation of the trigger signal by amplifier 44 that the audio signal continues to be produced. Preferably this time is adjusted to be around 4 seconds.

The output of one-shot flip-flop 54 is applied to a conventional trigger or gated oscillator 64 which includes operational amplifier 66. The frequency of the trigger oscillator 64 can be adjusted by variable oscillator 66 and is preferably set in the audio range at about 1000 Hz.

The output of differential amplifier 66 is amplified by conventional transistor amplifier 70 which includes transistor 72 and the output of this amplifier circuit is in turn applied to a conventional speaker 74 such as a set of earphones which produces an audio signal.

The circuitry illustrated in the drawing thus produces an audio output of the earphone 74 whenever the amplitude of the EEG signal exceeds the predetermined level set by resistor in the level detector 44 and whenever the EEG signal is in the frequency between roughly 2 Hz and 8 Hz. This audio signal produced at speaker 74 persists after the trigger signal is no longer produced by differential amplifier 44 for a time determined by variable resistor 60.

Many changes and modifications in the above-described embodiment of the invention can of course be carried out without departing from the scope thereof. Accordingly that scope is intended to be limited only by the scope of the appended claims.

What is claimed is:

1. Apparatus for suppressing an epileptic seizure comprising:
    electrical circuit means for receiving an EEG electrical waveform signal and producing an electrical trigger signal only when and for as long as the amplitude thereof exceeds a predetermined level with respect to a given reference level, that reference level indicating an epileptic seizure, electrical circuit means responsive to said trigger signal for producing an oscillatory electrical signal, until said trigger signal is no longer received, and only following production of said trigger signal, and speaker means for receiving said oscillatory signal and producing an audio signal which suppresses said seizure.

2. Apparatus as in claim 1 wherein said oscillatory signal producing means includes means for producing an audio frequency signal.

3. Apparatus as in claim 1 wherein said speaker means includes a set of earphones.

4. Apparatus as in claim 1 further including means for filtering out of an EEG signal components having a frequency greater than a first level and less than a second level and applying the filtered EEG signal to said receiving and trigger signal producing means.

5. Apparatus as in claim 4 wherein said filtering and applying means involves a high pass filter and a serially connected low pass filter.

6. Apparatus as in claim 4 wherein said first level is roughly 2 Hz and said second level is roughly 8 Hz.

7. Apparatus as in claim 4 further including a high impedance amplifier connected to the input to said filtering and applying means.

8. Apparatus as in claim 1 wherein said receiving and trigger signal producing means includes a level detector and wherein said oscillatory signal producing means includes a one-shot flip-flop connected to the output of said level detector and a trigger oscillator connected to the output of said flip-flop.

9. Apparatus as in claim 8 including a source of voltage and a variable resistor connected to said flip-flop for controlling the time duration of the pulse produced by said flip-flop.

10. Apparatus as in claim 8 wherein said level detector and trigger oscillator each include an operational amplifier.

11. Apparatus as in claim 8 further including an amplifier connecting said trigger oscillator to said speaker means.

12. Apparatus as in claim 8 wherein said level detector includes a differential amplifier with one input for receiving said EEG signal, a voltage source and a variable resistor connecting said voltage source to the other input of said differential amplifier.

13. Apparatus as in claim 1 wherein said oscillator signal producing means includes means for maintaining said oscillatory signal for a predetermined time following when said amplitude ceases to exceed said predetermined level.

14. Apparatus as in claim 13 wherein said oscillator signal producing means includes means for varying said predetermined time.

15. A method of suppressing epileptic seizures comprising the steps of producing an electrical trigger signal whenever the amplitude of an electrical EEG signal exceeds a predetermined level with respect to a predetermined reference level, that reference level indicating an epileptic seizure, producing an oscillatory electrical signal only following production of said trigger signal and converting said oscillatory signal into an audio, seizure suppressing signal.

16. A method as in claim 15 including the further step of maintaining said oscillatory signal for a predetermined time after said amplitude ceases exceeding said predetermined level.

17. A method as in claim 15 including the further step of removing components from said EEG signal having a frequency higher than a first frequency and less than a second frequency before producing said trigger signal.

* * * * *